United States Patent [19]

Suzuki

[11] Patent Number: 4,682,980
[45] Date of Patent: Jul. 28, 1987

[54] PUNCTURE NEEDLE ASSEMBLY

[75] Inventor: Tatsuo Suzuki, Yokohama, Japan

[73] Assignee: Terumo Corporation, Tokyo, Japan

[21] Appl. No.: 894,724

[22] Filed: Aug. 8, 1986

Related U.S. Application Data

[60] Continuation of Ser. No. 706,906, Mar. 1, 1985, abandoned, which is a division of Ser. No. 409,598, Aug. 19, 1982, abandoned.

[30] Foreign Application Priority Data

Aug. 19, 1981 [JP] Japan ............................ 56-129577
Dec. 8, 1981 [JP] Japan ............................ 56-198235

[51] Int. Cl.⁴ .................................................. A61M 5/00
[52] U.S. Cl. ................................. 604/122; 604/126; 604/411; 604/168
[58] Field of Search ............... 604/122, 126, 168, 411

[56] References Cited

U.S. PATENT DOCUMENTS

| | | |
|---|---|---|
| 3,055,361 | 9/1962 | Ballard . |
| 3,859,998 | 1/1975 | Thomas et al. ............... 604/168 |
| 4,193,399 | 3/1980 | Robinson ...................... 604/168 |
| 4,200,096 | 4/1980 | Charvin ........................ 604/168 |
| 4,207,870 | 6/1980 | Eldridge ....................... 604/168 |
| 4,269,186 | 5/1981 | Loveless et al. .............. 604/168 |
| 4,311,137 | 1/1982 | Gerard ......................... 604/122 |

Primary Examiner—C. Fred Rosenbaum
Assistant Examiner—Sherri E. Vinyard
Attorney, Agent, or Firm—Frishauf, Holtz, Goodman & Woodward

[57] ABSTRACT

In general, the confirmation of a puncture in a blood vessel is made through a visual check of flush back of the blood from the blood vessel into a puncture needle assembly. The conventional puncture needle assembly incorporates a membrane filter permeable to air but impermeable to blood, in order to prevent the blood from flooding outside. The conventional puncture needle, however, cannot be used suitably for the puncture of a blood vessel deep in the tissue. In the puncture needle assembly of the invention, an air relief opening is formed in a portion of a puncture needle hub, catheter hub or an end plug attachable to the puncture needle hub or the catheter, hub other than the portion which constitutes a pressing surface on which the thumb of the user is placed to exert a thrust force for puncturing the tissue and the blood vessel, as in the case of ordinary syringes. The air in the puncture needle and in the puncture needle hub is relieved through the air relief opening, thus to permit smooth flush back of the blood.

9 Claims, 27 Drawing Figures

FIG. 4b  FIG.4a
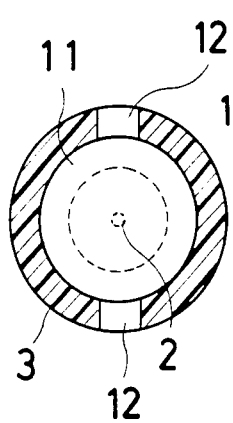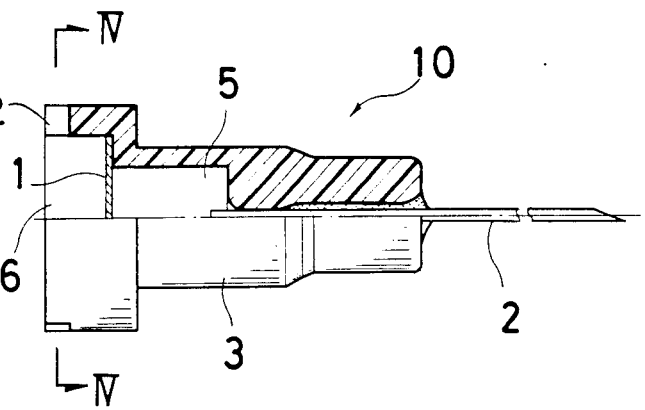
FIG. 5b  FIG.5a
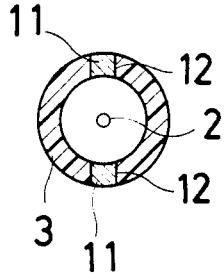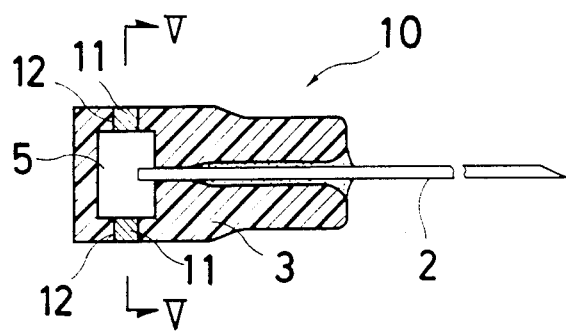
FIG. 8
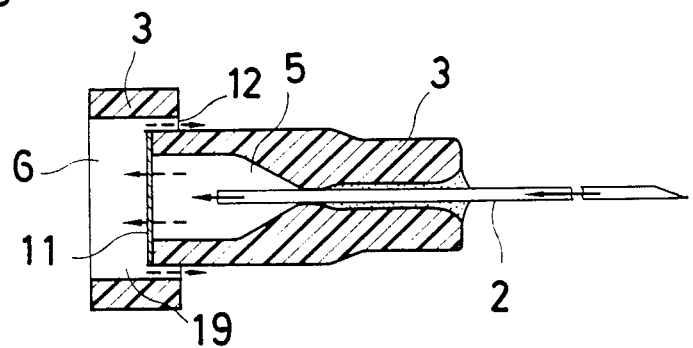

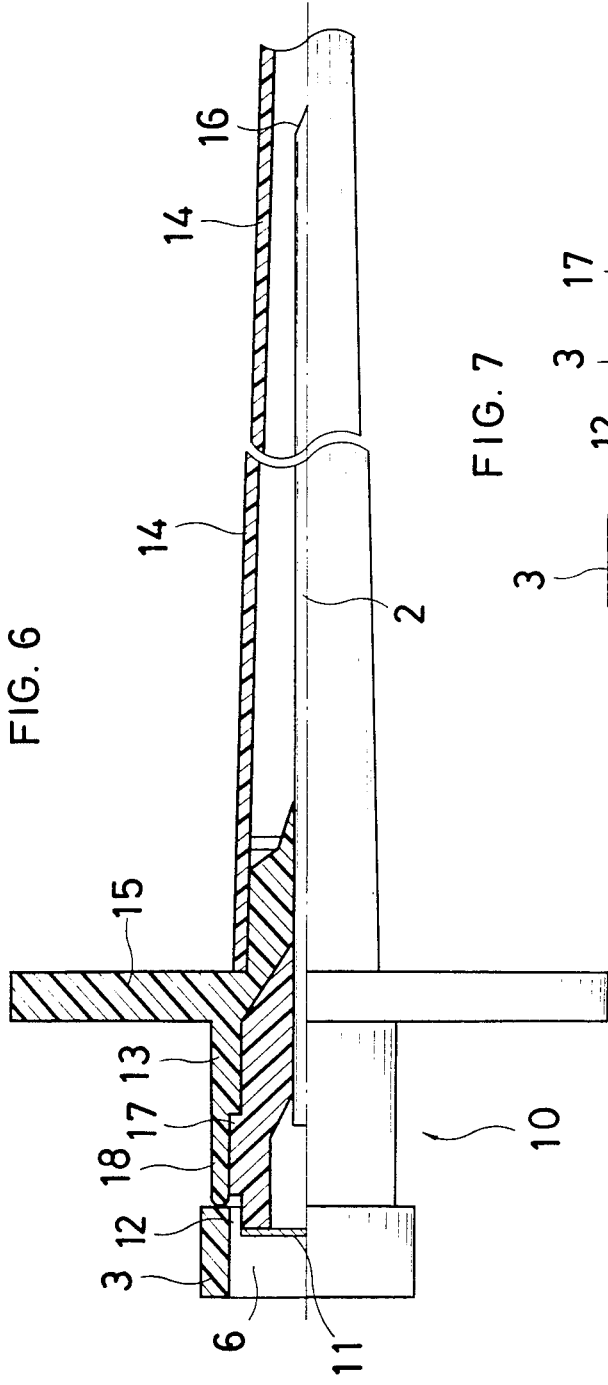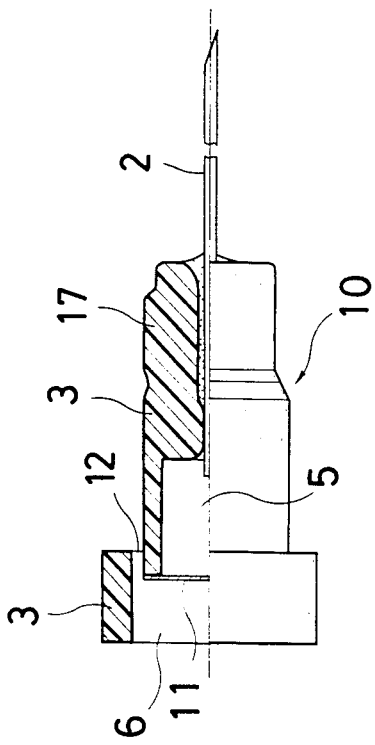

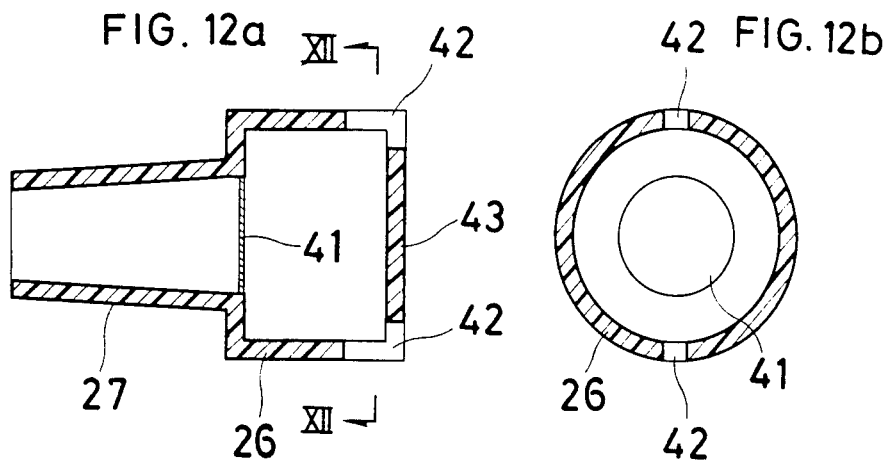
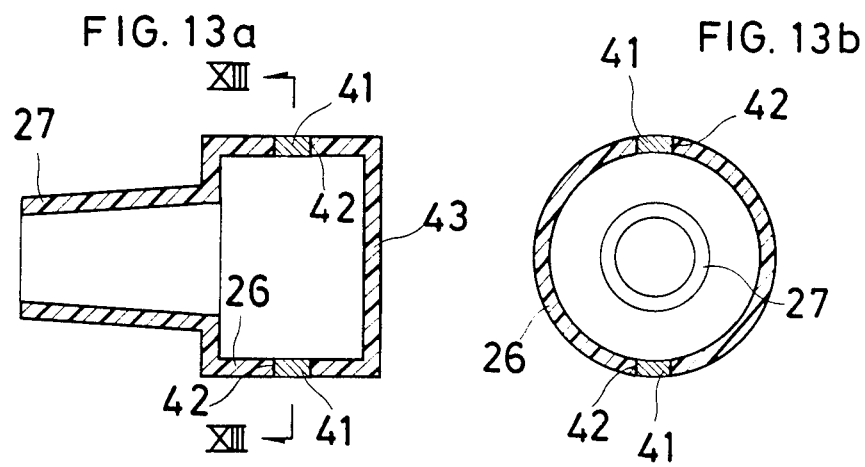
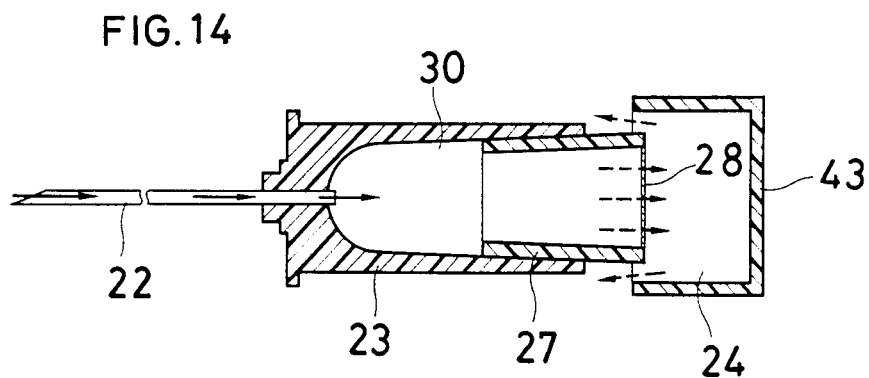

PUNCTURE NEEDLE ASSEMBLY

This application is a continuation of application Ser. No. 706,906, filed 3-1-85, which is in turn a divisional of application Ser. No. 409,598, filed 8-19-82, both now abandoned.

BACKGROUND OF THE INVENTION

1. Field of the Invention

The present invention relates to a puncture needle assembly provided with a puncture needle hub or a detachable end plug assigned and constructed to permit the flush back of blood during puncture of an artery or the like regardless of the positions of fingers.

2. Description of the Prior Art

When the tip of a puncture needle is correctly positioned in the desired blood vessel, especially an artery, the blood flows back into a transparent or translucent hub of the puncture needle due to the blood pressure through the inner bore of the puncture needle. This phenomenon is generally referred to as "flush back". The confirmation of the fact that the tip of the puncture needle is correctly located in the blood vessel is made through a visual check of the flush back of the blood. If the tip of the puncture needle hub opens, the flushing blood will come out of the puncture needle hub undesirably.

Alternatively, U.S. Pat. No. 3,055,361 discloses a structure wherein a catheter hub and vent plug are provided at both interfaces thereof with at least one mating vent groove, so that alignment of these grooves due to the relative rotation of the catheter hub and the vent plug if required ensures escape of air contained. However, this structure has drawbacks in that after air purge relative turning of the two elements out of alignment of the grooves is required, otherwise the blood would leak out of the grooves. In order to obviate this inconvenience, such a puncture needle assembly has been developed as having a detachable air vent plug which is opened at its end and provided with a membrane filter or the like permeable only to the air and adapted to prevent the blood from passing therethrough, the air vent plug and the puncture needle hub cooperating with each other in defining therebetween a small chamber communicated with the inner bore of the puncture needle. In puncturing a blood vessel, the air in the puncture needle and the small chamber is forced out through the membrane filter while the blood is allowed to flush back into the small chamber. In this puncture needle assembly, the hub has a rectangular parallelopiped shape. In use, the puncture needle is pushed to puncture the tissue and the blood vessel with the puncture needle hub pinched at its opposite side surfaces parallel to the puncture needle by the first finger (thumb) and the second finger (forefinger). This puncture needle assembly is suitable for the puncture of a blood vessel which is comparatively shallow in the tissue, e.g. veins, because in such a case only a small force is required for the puncture. However, with the manner of pinching of the hub stated above, it is quite difficult to correctly puncture a blood vessel which is deep in the tissue, e.g. arteries, because in such a case a large force is required to penetrate the tissue. This difficulty is encountered, for example, when a seldinger needle, which is used for inserting an angiography catheter into an artery or when a puncture needle for securing an artery, is driven into the latter. In such cases, the needle encounters a large resistance due to the elasticity of the artery or the tightness of the tissue. The seldinger needle or the puncture needle consists of two or three members including a catheter, inner needle or a dilator. In puncturing, the inner needle hub is held by a hand and, a catherter hub and the dilator hub are also held so that they may move together with the inner needle. As stated before, the puncturing requires a large force and, hence, is extremely difficult to conduct if the hubs are pinched at opposite side surfaces by the first finger (thumb) and the second finger (forefinger).

To overcome this problem, it has been proposed to provide the catheter hub with two flanges so that the puncture needle assembly may be held by three fingers: namely, the second finger (forefinger) retained on one flange, third finger (middle finger) retained on the other flange and the first finger (thumb) placed on the end of the puncture needle hub. This arrangement of fingers, identical to that in the use an of ordinary syringe, permits a comparatively easy puncture. This proposal, however, cannot be applied to the aforementioned puncture needle assembly in which the hub is opened only at its end, because the opened end is closed completely by the bulb of the thumb to prevent the air in the needle and the small chamber from being relieved. In consequence, the blood cannot flush back into the small chamber so that the correct puncture cannot be confirmed visually. In addition, this type of puncture needle assembly cannot be used in combination with another instrument such as a syringe because of the presence of a filter in the opening of the puncture needle. In consequence, the users have been obliged to use other means.

SUMMARY OF THE INVENTION

Accordingly, a first object of the invention is to provide a puncture needle assembly, particularly a novel construction of the inner needle hub, which can realize assuredly the visual confirmation of the flush back of the blood even when the puncture needle is used for blood vessels running deep in the tissue to require a large force for the penetration.

A second object of the invention is to provide a puncture needle assembly provided with an end plug and having a large variety of use, which can allow of the visual confirmation of the flush back even when the puncture needle is applied to a blood vessel running deep in the tissue to require a large force for the penetration.

According to an aspect of the invention, there is provided a puncture needle assembly comprising: a catheter; a hollow catheter hub fixed to one end of the catheter and having a hollow chamber communicating with the inside of the catheter; a hollow inner needle insertable and withdrawable into and out of the catheter through the internal cavity of the catheter hub, the inner needle having a beveled point adapted to be positioned to project at the other end of the catheter; and a transparent or translucent inner needle hub and fixed to the base proximal end portion of the inner needle; wherein the inner needle hub is provided at its end opposite to the inner needle with a catheter pressing surface and has a passage providing a communication between the internal cavity of the inner needle and the atmosphere through an opening or openings formed in a portion of the inner needle hub other than the pressing surface; the puncture needle assembly further comprises an air-permeable blood-tight member disposed in the passage, the internal cavity of the inner needle being communicated with the atmosphere through the air-permeable blood-tight member.

The air-permeable blood-tight member can be made of a material which permits air to permeate but prevents blood from passing therethrough, and may be constituted by, for example, a member having a filter or slit or slits. The opening or openings may be formed in the peripheral wall of the inner needle hub. Alternatively, the inner needle hub is made to have two cylindrical portions of different diameters: namely a smaller-diameter portion closer to the inner needle and a larger-diameter portion connected to the smaller-diameter portion, and the opening or openings is formed in the axial end surface of the larger-diameter portion closer to the tip of the inner needle. In order to obtain a fixed orientation of the edge beveled surface of the inner needle, the inner needle hub and the catheter hub are preferably provided with mating fitting portions. It is also preferred to provide the catheter hub with a flange for supproting by fingers during the puncturing operation.

According to a second aspect of the invention, there is provided a puncture needle assembly comprising a puncture needle provided with a through bore, a transparent or translucent puncture needle hub fixed to the end of the puncture needle opposite to the beveled point, and an air vent plug adapted to be connected to the puncture needle hub detachably and in a liquid-tight manner, wherein the air vent plug is provided at its end surface opposite to the puncture needle with a pressing surface and adapted to form, when it is attached to the puncture needle hub, a passage providing a communication between the through bore in the puncture needle and the atmosphere, the passage being opened to the atmosphere through an opening or openings formed in a portion of the air vent plug other than the pressing surface, the puncture needle assembly further comprising an air-permeable blood-tight member disposed in the passage, the through bore in the puncture needle being communicated with the atmosphere through the air-permeable blood-tight member.

According to another form of the second aspect of the invention, there is provided a puncture needle assembly comprising a puncture needle having a through bore, a puncture needle hub fixed to the end of the puncture needle opposite to the beveled point, an air vent plug adapted to be connected to the puncture needle hub detachably and in a liquid-tight manner, an outer catheter having a through bore for receiving the puncture needle, and a catheter hub fixed to the proximal end of the outer catheter and attachable to the puncture needle hub, wherein the air vent plug is provided at its end opposite to the puncture needle hub with a pressing surface and is adapted to form, when it is attached to the puncture needle hub, a passage providing a communication between the through bore of the puncture needle and the atmosphere, the passage being opened to the atmosphere through an opening or openings formed in a portion at least other than the pressing surface, the puncture needle assembly further comprising an air-permeable blood-tight member disposed in the passage, the through bore in the puncture needle being communicated with the atmosphere through the air-permeable blood-tight member.

The air-permeable blood-tight member can be made of a material which permits air to permeate but prevents blood from passing therethrough, and may be constituted by, for example, a member having a filter or slit or slits. The opening may be formed in the peripheral wall of the inner needle hub. Alternatively, the inner needle hub is made to have two cylindrical portions of different diameters: namely a smaller-diameter portion closer to the inner needle and a larger-diameter portion connected to the smaller-diameter portion, and the opening or openings is formed in the axial end surface of the larger-diameter portion closer to the beveled point of the inner needle.

BRIEF DESCRIPTION OF THE DRAWINGS

FIG. 1a is a partial sectional view of a conventional puncture needle;

FIG. 1b is a sectional view taken along the line I—I of FIG. 1a;

FIG. 2a is a partial sectional view of a puncture needle assembly in accordance with a first form of a first embodiment of the invention;

FIG. 2b is a sectional view taken along the line II—II of FIG. 2a;

FIG. 3a is a partial sectional view of a second form;

FIG. 3b is a sectional view taken along the line III—III of FIG. 3a;

FIG. 4a is a partial sectional view of a third form;

FIG. 4b is a sectional view taken along the line IV—IV of FIG. 4a;

FIG. 5a is a partial sectional view of a fourth form;

FIG. 5b is a sectional view taken along the line V—V of FIG. 5a;

FIG. 6 is a partly-sectioned side elevational view of an angiography introduction needle to which the puncture needle assembly of the first embodiment is applied;

FIG. 7 is an enlarged partly sectioned side elevational view of a puncture needle assembly of the first embodiment applied to an angiography introduction needle;

FIG. 8 is a sectional view of the puncture needle assembly in accordance with a first embodiment of the invention, for explaining the operation of the first embodiment;

FIG. 10a is a sectional view of a first form of an air vent plug incorporated in a puncture needle assembly in accordance with a second embodiment of the invention;

FIG. 10b is a sectional view taken along the line X—X of FIG. 10a;

FIG. 11a is a sectional view of a second form;

FIG. 11b is a sectional view taken along the line XI—XI of FIG. 11a;

FIG. 12a is a sectional view of a third form;

FIG. 12b is a sectional view taken along the line XII—XII of FIG. 12a;

FIG. 13a is a sectional view of a fourth form;

FIG. 13b is a sectional view taken along the line XIII—XIII of FIG. 13a;

FIG. 14 is a sectional view of the puncture needle assembly of the second embodiment, for explaining the operation of the second embodiment;

FIG. 17b is a sectional view taken along the line XVII—XVII of FIG. 17a.

DETAILED DESCRIPTION OF THE PREFERRED EMBODIMENTS

A puncture needle assembly according to the first aspect of the invention will be described in detail hereinunder with reference to FIGS. 1 thru 8.

Before turning to the detailed description of the first aspect of the invention, an explanation will be made hereinunder as to the conventional puncture needle with specific reference to FIGS. 1a and 1b, to clarify the problems of the prior art for an easier understanding of the advantageous features of the invention.

Figures 1A, 1B:
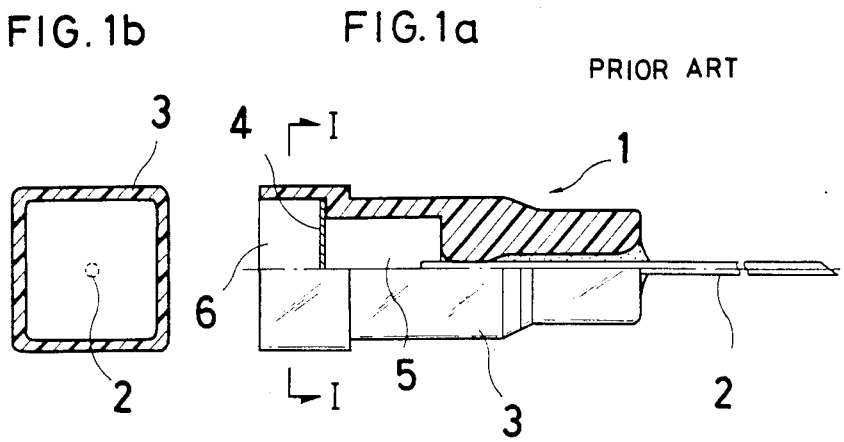

Referring to FIG. 1a, a typical conventional puncture needle assembly 1 has a puncture needle 2 and an inner needle hub 3 made of a transparent material. As shown in FIG. 1b, the inner needle hub 3 has a rectangular outer configuration or cross-section. A small chamber 5 is defined within the hub 3 by a filter 4 which is permeable to air but not permeable to body fluid. In use, the puncture needle assembly 1 is pinched at opposite side surfaces of the parallelopiped hub and is thrusted to puncture a blood vessel. In consequence, the blood is flushed back into the small chamber 5 through the inner needle 2 so that the puncture of the blood vessel is confirmed visually. Meanwhile, the air in the inner needle 2 and the small chamber 5 is relieved through the filter 4 and is discharged to the atmosphere through the open end 6 of the hub 3 so as to allow the blood to flush back into the small chamber 5. This conventional puncture needle assembly, however, encounters the problems as stated before.

These problems, however, are overcome by the puncture needle assembly 10 in accordance with a first aspect of the invention as will be understood from the following description of several examples thereof. The problems encountered by the conventional puncture needle assembly is attributable to the fact that, when the assembly is used for puncturing a blood vessel deep in the tissue, the air cannot be relieved to the outside because the open end 6 of the hub 3 is closed by the thumb which has to exert a large force to overcome the penetration resistance, so that the air pressure in the space between the filter 4 and the thumb is increased to prevent the flush back of the blood.

To obviate this problem, according to the first aspect of the invention, the puncture needle assembly has an air-permeable blood-tight member 11 which permits the air to be relieved therethrough but does not permit the blood or other body fluid to pass therethrough. Therefore, even when the open end of the puncture needle hub is closed during the operation, the air in the puncture needle and the small chamber is forced out through the air-permeable blood-tight member 11. The air is then discharged to the outside through at least one opening 12 formed in the hub 3. Therefore, the air is allowed to flush back into the small chamber. Since the puncture needle hub 3 is transparent or translucent, the flush back of the blood can be easily confirmed by a visual check. The air-permeable blood-tight member may be constituted by a filter or a member having at least one slit. The filter may be a membrane filter composed of a substrate of a polyester resin coated with polyvinyl chloride or may be a sintered body. The member with at least one slit is preferably made of a hydrophobic material such as polypropylene to cope with both the demands for air permeability and blood impermeability. In order to ensure the impermeability to blood, the size of the slit is selected to fall between 0.1 and 20 μm.

Figures 2A, 2B:
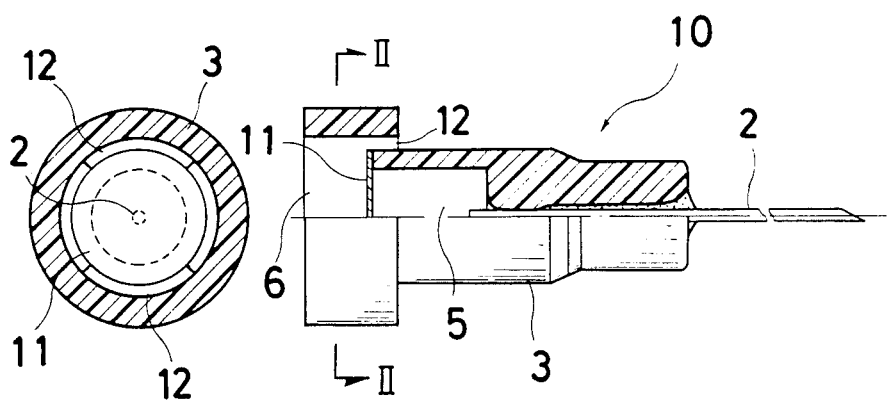

Referring now to FIGS. 2a and 2b, in a first form of the puncture needle assembly in accordance with the first aspect of the invention, a small chamber 5 for confirmation of the flush back is defined within the puncture needle hub 3, by the air-permeable blood-tight member 11 consisting of a filter or a member with at least one slit permeable to air but impermeable to blood. The aforementioned opening 12 is forxed at the downstream side of the small chamber 5 as viewed in the direction of flow of air or blood during flushing back. More specifically, in this form, the puncture needle hub 3 is constituted by two cylindrical portions of different diameters: namely, a smaller-diameter portion adjacent to the puncture needle and a larger-diameter portion connected to the smaller-diameter portion, and the opening 12 is formed in the axial end surface or the larger-diameter portion closer to the beveled point of the needle. As will be understood from FIG. 2b which is a sectional view taken along the line II—II of FIG. 2a, the opening 12 is formed in at least a portion of the aforementioned end surface of the puncture needle hub.

Figures 3A, 3B:
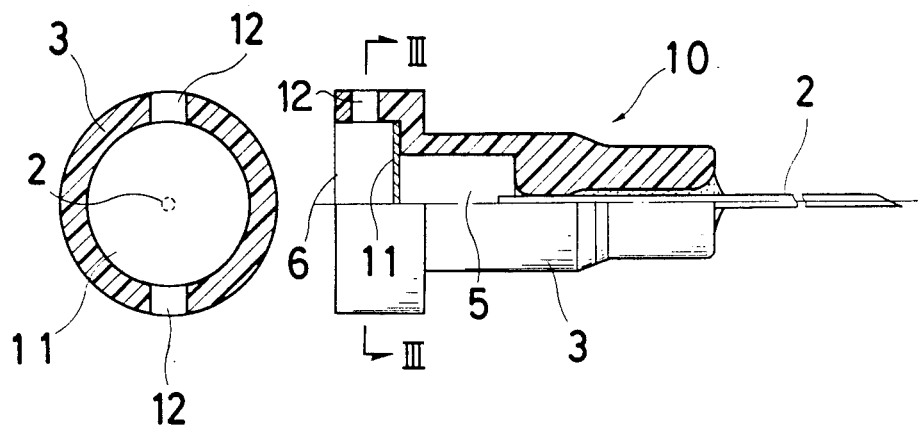

FIGS. 3a and 3b show another form of the puncture needle assembly of the first aspect. A small chamber 5 for confirmation of flush back of the blood is formed within a passage defined in the puncture needle hub 3. The opening 12 is formed at the downstream side of the small chamber 5. More specifically, in this case, the opening 12 is formed in the peripheral wall of the puncture needle hub 3 to penetrate the same radially. As will be understood from FIG. 3b which is a sectional view taken along the line III—III of FIG. 3a, the opening 12 is formed at least in a portion of the peripheral wall of the puncture needle hub 3.

In still another form shown in FIGS. 4a and 4b, the opening 12 is provided in the form of a groove in the downstream-side end surface of the puncture needle hub 3 opposite to the puncture needle, i.e. in the catheter pressing surface. As will be understood from FIG. 4b which is a sectional view taken along the line IV—IV of FIG. 4a, the opening 12 may be formed in at least a portion of the outer peripheral wall of the proximal end portion of the puncture hub 3.

FIGS. 5a and 5b show a further form in which the air-permeable blood-tight member 11 and the opening 12 are located substantially at the same position. Namely, the air-permeable blood-tight member 11 is provided in the opening 12 of the passage 7 formed in the puncture needle hub 3, while the proximal end of the puncture needle hub 3 is closed. As will be understood from FIG. 5b which is a sectional view taken along the line V—V, the opening 12 may be provided at least in a portion of the peripheral wall of the puncture needle hub 3, and the air-permeable blood-tight member 11 can have any suitable thickness.

As explained in the introductory part of this specification, the puncture needle hub 10 of the invention is adapted for use in combination with a catheter 13. This combination is illustrated in FIG. 6 in which the upper half part is shown in section. The puncture needle assembly of the invention is inserted into an outer catheter 13 on which is fitted protector 14 for ensuring safety and sanitation. For putting the assembly into use, the protector 14 is detached and the assembly is thrusted by the first finger (thumb) put on the open end 6 of the puncture needle hub 3 while the second finger (forefinger) and the third finger (middle finger) are retained by a flange 15, to penetrate into the tissue thereby to puncture the blood vessel. Although the open end 6 of the hub 3 is closed, the air can be relieved through the opening 12 mentioned before, so that the flush back of the blood can be visualy confirmed without fail if the blood vessel is correctly punctured. After the confirmation of the flush back, the puncture needle is gently withdrawn while the catheter hub is clamped, and thus the puncture needle is fully withdrawn. Meanwhile, the portion of the skin around the punctured portion is pressed by fingers. Then, an angiography catheter is introduced into the catheter which remains in the blood vessel or a syringe is connected to the same.

For puncturing a blood vessel burried deep in the tissue, particularly an artery having a high elasticity, it is preferred that the tapered beveled edge surface 16 of the puncture needle 2 is orientated always in a constant direction. To cope with this demand, in the puncture needle assembly of the invention, it is preferred to provide mating ridge 17 and groove 18 in two members fitting each other. In the form shown in FIGS. 6 and 7, a locking ridge 17 is formed on the puncture needle hub 3 while a mating groove 18 is formed in the catheter hub. These ridge 17 and groove 18 fit each other to prevent the puncture needle hub 3 and the catheter hub from rotating relatively to each other, so that damage of blood vessel which may for otherwise be caused by a rotation of the puncture needle is avoided and, at the same time, the orientation of the beveled surface of the needle in the blood vessel can be confirmed easily.

The operation of the puncture needle assembly in accordance with the first aspect of the invention will be described hereinunder with specific reference to FIG. 8.

When a blood vessel is punctured by the puncture needle of the first aspect, the blood flows into the small chamber 5 defined as required by the air-permeable blood-tight member 11 within the passage 7 in the puncture needle hub through the internal bore of the puncture needle 2 as indicated by a solid-line arrow, while forcibly displacing the air out of the puncture needle 2 and the small chamber 5 through the air-permeable blood-tight member 11 as indicated by broken-line arrows. The air is then discharged to the atmosphere through the space 19 in the puncture needle hub passage 7 and then through the opening 12. Therefore, the air residing in the puncture needle 2 and the small chamber 5 do not prevent flush back of the blood. In addition, since the hub 3 is made of a transparent material, the blood flushing back into the small chamber 5 can be visually checked to permit the confirmation of the fact that the desired blood vessel in the tissue is punctured correctly by the puncture needle 2.

In the puncture needle of the first aspect of the invention, the puncture needle hub is provided at its end surface opposite to the puncture needle with a catheter pressing surface and a passage communicating with the internal bore of the puncture needle, the passage opening to the atmosphere through an opening which is formed at least in a surface different from the pressing surface. In addition, an air-permeable blood-tight member is disposed in the above-mentioned passage so that the air in the internal bore of the puncture needle is communicated with the atmosphere through the air-permeable blood-tight member. The pressing surface constitutes an open end surface of the puncture needle hub. Therefore, even though the open end of the puncture needle hub is closed by the thumb during the puncturing operation, the air is easily and smoothly relieved from the inner bore of the puncture needle and the puncture needle hub through the air-permeable blood-tight member so that the blood is allowed to flush back into the small chamber. The puncture needle hub made of a transparent or translucent material permits an easy visual check of the blood flushing back through the passage therein, so that it is possible to confirm that the puncture needle and, hence, the catheter surrounding the needle correctly catch and puncture the desired blood vessel in the tissue. The air-permeable blood-tight member may be a membrane filter or a slit-equipped member which is easy to manufacture. The puncture operation is facilitated by providing the catheter hub with a flange. The pressing of the open end 6 of the puncture needle hub by the thumb is made when a comparatively large thrusting force is required, i.e. when the needle aims at a blood vessel deep in the tissue, particularly an artery. It will be understood that the problem concerning the operation of the conventional puncture needle assembly can be completely eliminated by the puncture needle assembly of the invention with relatively simple construction.

Furthermore, the fitting and aligning mechanism provided on the puncture needle assembly of the invention as shown in FIGS. 6 and 7 makes it possible to provide a constant orientation of the beveled surface of the puncture needle so that any damage of the blood vessel which may otherwise be caused by rotation of the needle during puncture is fairly avoided and the orientation of the beveled surface in the blood vessel can be confirmed easily.

Figure 9:
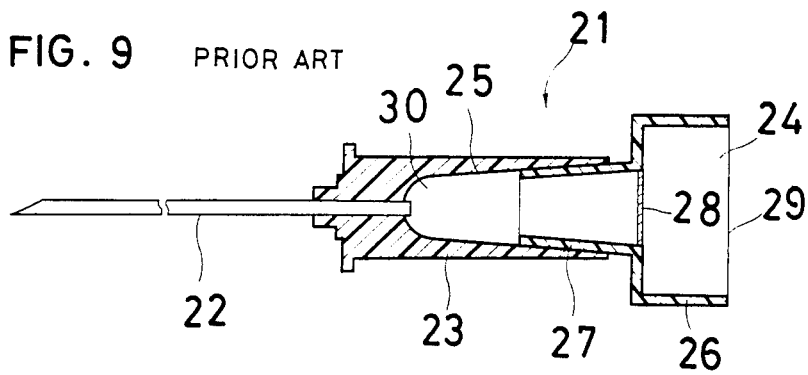
FIG. 9 is a partial sectional view of a conventional puncture needle assembly.

FIG. 9 is a partial sectional view of a conventional puncture needle assembly 21. This conventional puncture needle assembly 21 has a puncture needle 22, a puncture needle hub 23 fixed to the end of the needle 22 opposite to the beveled point of the needle and an air vent plug 24 adapted to be mounted to the hub detachably and in a liquid-tight manner. The puncture needle hub 23 has a circular cross-section. A circular-cross-sectioned tapered bore 25 in the puncture needle 22 at its one end communicates with a through bore (not shown) of the puncture needle, 23 and at its other end is attachable to a cylindrical projection 27 projecting from the proximal end portion 26 of the air vent plug 24. A membrane filter 28 permeable to air but impermeable to blood is attached to the boundary between the proximal end portion 26 and the projection 27, and the end 29 of the base portion 26 is opened. The end of the projection 27 also is opend so that, when the air vent plug 24 is attached to the puncture hub 23 in the manner shown in FIG. 9, a small chamber 30 is defined by the puncture needle hub 23, projection 27 and the membrane filter 28. In use, the puncture hub 23 is pinched at its opposing side surfaces and the assembly is thrusted to puncture the blood vessel so that the blood flushes back into the small chamber 30 through the internal bore of the puncture needle 22 to permit a visual confirmation of the exact puncture of the blood vessel. Meanwhile, the air in the puncture needle 22 and the small chamber 30 is relieved through the filter 28 and is discharged through the open end 29 of the base portion 26 of the air vent plug 24 to permit the flush back of the blood. This conventional puncture needle, however, encounters the problem as stated before.

Several forms of puncture needle assembly in accordnace with the second aspect of the invention, capable of overcoming the above-described problem will be explained hereinunder with reference to the accompanying drawings. The aforementioned problem of the prior art is attributable to the fact that, since the conventional puncture needle assembly is thrusted by the thumb put on the open end 29 of the air vent plug 24 when puncturing a blood vessel buried deep in the tissue, the opening in the open end 29 is completely closed to prevent air from being discharged so that the air pressure in the space between the filter 28 and the thumb is increased to resist to the flush back of the blood. To obviate this problem, according to the invention, an air-permeable blood-tight member 41, adapted to permit the air to permeate but prevent the body fluid such as blood to pass therethrough, is disposed in a passage intercommunicating the inner through bore of the puncture needle and the atmosphere. The air relieved through this air-permeable blood-tight member 41 is then discharged to the outside through an opening 42 formed in the air vent plug 24, thereby to permit the flush back of the blood. The puncture needle hub 23 which is transparent or translucent permits an easy visual confirmation of the blood flushing back into the puncture needle hub 23. Any material permeable to air but impermeable to blood can be used as the material of the air-permeable blood-tight member 41. The member 41, for example, may be constituted by a filter or a member provided with at least one slit. As the filter, a membrane filter composed of a substrate of polyester resin coated with polyvinyl chloride or a sintered body can be used practically because such materials exhibit good blood-tightness or impermeability and are available at moderate cost. When a member with at least one slit is used as the air-permeable blood-tight member, a hydrophobic material such as polypropylene is used as the material in order to obtain high air-permeability and blood-tightness or impermeability, and, for assuring a good blood-tightness or impermeability, the gap of the slit is selected preferably to range between 0.1 and 20 μm. When the filter is used as the air-permeable blood-tight member 41, it is formed separately from the air vent plug 24 and then fitted in the latter. However, when the member with slits is used, it can be formed as a unit with the air vent plug advantageously.

Several forms of this second aspect of the invention will be described hereinunder. The description will be focussed on the construction of the air vent plug, because the other portions of these forms are substantially identical. Needless to say, these air vent plugs are used in combination with the puncture needle assembly shown in FIG. 9. Preferably, the puncture needle 23 has a tapered bore 25 communicating with the through bore in the puncture needle 22. This arrangement smooths the flow of the flushing back blood so that the deposition of fibrin or blood clot attributable to hemolysis or coagulation is avoided effectively. The puncture needle hub 23 may be rectangular parallelopiped, clindrical or other suitable form. The outer peripheral surface of the puncture needle hub 23 may be provided with ribs or the like to facilitate the holding by hand. Although the air vent plug 24 is described to have a cylindrical form, it can have any desired shape provided that such shape permits a liquid-tight fit of the air vent plug 24 in the puncture needle hub 23. For instance, the air vent plug can have a tapered form complimentary to the tapered form of the puncture needle hub 23.

Various forms of the second aspect of the invention have the following common feature. Unlike the conventional puncture needle assembly in which the end of the air vent plug 24 opposite to the beveled point is opened, the same end of the air vent plug 24 in the puncture needle of the second aspect is fully closed to constitute a pressing surface 43 on which the thumb is put to exert the thrusting force. In addition, an opening 42 for relieving air is provided at the downstream side of the air-permeable blood-tight member as viewed in the direction of flow of the blood and air during puncturing. In order that the air can smoothly escape through the opening 42, the opening 42 is provided at least in the surface of the air vent plug 24 other than the pressing surface 43. The pressing surface 43, however, need not always be closed but may be left opened as shown in FIG. 9. All that is necesary is that the opening 42 is provided at such a portion as would permit a smooth relief of air displaced by the flushing back blood even when the puncture is made by driving the assembly by the thumb pressed on the end 29 of the air vent plug 24.

Figures 10A, 10B:
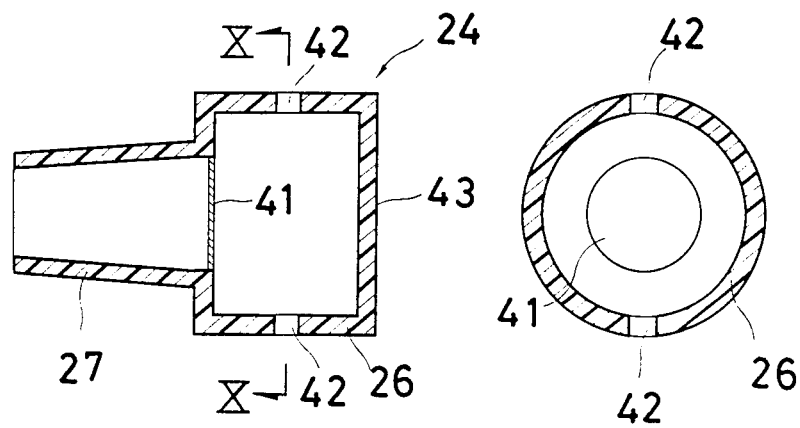

In one form of the second aspect of the invention shown in FIGS. 10a and 10b, the opening 42 is formed in the peripheral wall of proximal end portion 26 of the air vent plug 24 downstream from the air-permeable blood-tight member 41 disposed at the juncture between the proximal end portion 26 and the projection 27. As will be understood from FIG. 10b which is a sectional view taken along the line X—X of FIG. 10a, at least one opening 42 formed in the peripheral wall of the air vent plug 24 suffices. In the illustrated example, the proximal end portion 26 has a shape different from the projection 27 in order to provide a sufficient large area of the end surface constituting the pressing surface 43. Needless to say, however, the proximal end portion 26 may be formed as an extension of the projection 27 provided that the opening 42 is formed in the peripheral wall. In the example illustrated in FIGS. 10a and 10b, the pressing surface 43 may be opened as in the case of the prior art shown in FIG. 9.

Figures 11A, 11B:
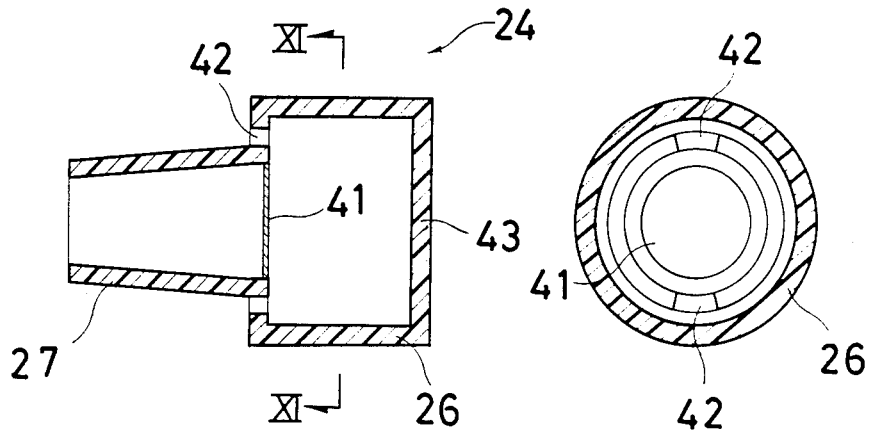

In another form shown in FIGS. 11a and 11b, the proximal end portion 26 of the air vent plug 24 is made to have a larger diameter than the projection 27 such that a step or shoulder is formed therebetween. The opening 42 is formed in the end surface of the step facing the beveled point of the needle at the downstream side of the air-permeable blood-tight member 41 which is disposed in the same manner as that in the example shown in FIGS. 10a,10b. As will be seen from FIG. 11b which is a sectional view taken along the line XI—XI of FIG. 11B, the opening 42 may be formed in at least a portion of the end surface of the step. In the example shown in FIGS. 11a,11b the pressing surface 43 may be opened as in the prior art shown in FIG. 9.

In still another form shown in FIGS. 12a and 12b, the opening 42 is formed to extend over the peripheral wall and the pressing surface 43 of the air vent plug 24, at the downstream side of the air-permeable blood-tight member which is mounted in the same manner as that shown in FIGS. 10a,10b. During the puncturing, although the portion of the opening 42 residing in the end surface 43 is closed by the thumb, other portion of the opening 42 is left opened to permit the air to escape therethrough. Thus, the invention does not exclude the modification in which the opening is formed at the juncture between the end surface and the peripheral surface of the air vent plug. As will be understood from FIG. 12b which is a sectional view taken along the line XII—XII of FIG. 12a, the opening 42 may be formed in at least a portion of the juncture between the end surface 43 and the peripheral wall of the air vent plug 24. In this form of the puncture needle assembly shown in FIGS. 12a,12b, the end surface 43 of the air vent plug 24 may be opened as in the case of the prior art shown in FIG. 9.

In a further form of the second aspect of the invention shown in FIGS. 13a and 13b, the opening 42 is formed substantially at the same position as the air-permeable blood-tight member 41. Namely, the air-permeable blood-tight member 41 is disposed in the opening 42 formed in the peripheral wall of the proximal end portion 26 of the air vent plug 24. Such a modification is fairly involved by the present invention. As will be understood from FIG. 13b which is a sectional view taken along the line XIII—XIII of FIG. 13a, the opening 42 may be formed in at least a portion of the member mentioned above as in the case of preceding forms shown in FIGS. 10a turn 12b. Also, the air-permeable blood-tight member 41 placed in the opening 42 can have a suitable thickness.

An explanation will be made hereinunder as to the operation of the puncture needle assembly of the second aspect, with specific reference to FIG. 14. As will be seen from this Figure, the puncture needle assembly of the second aspect of the invention is pinched at both sides of the puncture needle hub 23 by the second finger (forefinger) and the third finger (middle finger) while the first finger (thumb) is put on the end surface 43 of the air vent plug 24 which may be opened, and a thrusting force is exerted by the thumb to puncture a blood is vessel. In consequence, the blood flushed back into the small chamber 30 through the inner bore of the puncture needle 22 as indicated by a solid-line arrow. As a result, the air in the puncture needle 22 and the small chamber 30 are forced out by the flushing back blood through the air-permeable blood-tight member 41 as indicated by broken-line arrow. The air is then discharged to the outside (atmosphere) through the opening 42 through the space in the proximal end portion of the air vent plug 24 as indicated by broken-line arrows. It will be seen that the puncture needle assembly of this second aspect of the invention is entirely free from the problem of prevention of blood flush back due to confinement of air in the small chamber 30 which is inevitable in the conventional puncture needle assembly shown in FIG. 9. In addition, the hub 23 made of a transparent material permits a visual check of the blood flushing back to the small chamber 30, so that it is possible to confirm the exact puncture of the desired blood vessel in the tissue. This puncture needle assembly of the second aspect can be used in combination with a catheter as a catheter insertion device which has an outer catheter 44 capable of receiving the puncture needle 22 and a catheter hub 45 fixed to one end of the outer catheter and attachable to the puncture needle hub (See FIG. 15).

Figure 15:
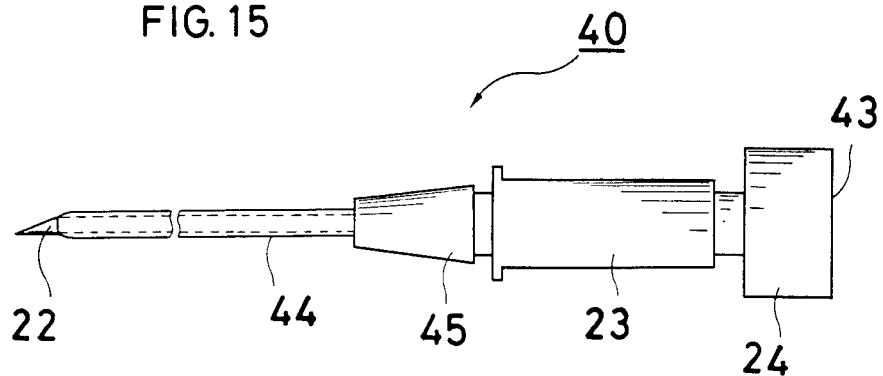
FIG. 15 is a side elevational view of another example of use of the puncture needle assembly in accordance with the second embodiment.

In either one of the arrangement shown in FIGS. 14 and 15, the puncture needle is used as an assembly. In the arrangement shown in FIG. 14, for making a selective angiographic operation, the air vent plug 24 is detached from the puncturing needle hub 23 after confirming the flush back of the blood as stated before, and a guide wire (not shown) is introduced into the blood vessel through the puncture needle 22. Upon reaching the blood vessel, the guide wire is held stationary and the puncture needle 22 solely is withdrawn while preventing the leakage of the liquid by, for example, pressing the area of the skin around the puncture. It is thus possible to introduce the guide wire into the blood vessel with the minimum bleeding.

For making the outer catheter indwell in the blood vessel, the puncture can be easily made even to the portion of the body where the resistance by the tissue is large, by arranging the assembly in the manner shown in FIG. 15. In some cases, the puncture needle 22 is used in combination with a syringe. In such a case, the air vent plug 24 is detached from the puncture needle plug 23 and the syringe is connected to the puncture needle hub 23 in place of the air vent plug 24.

Figure 16:
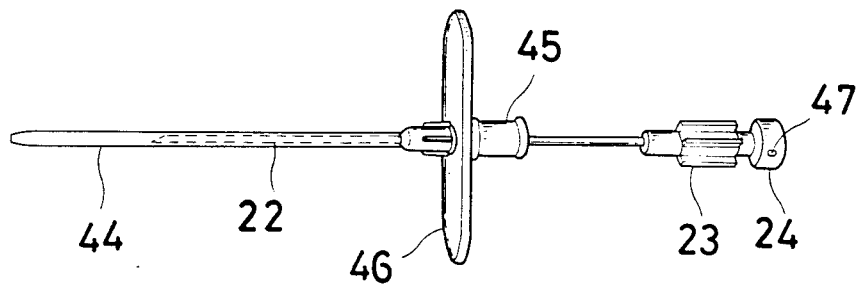
FIG. 16 is a perspective view of still another example of use of the puncture needle assembly of the second embodiment.
Figure 17A:
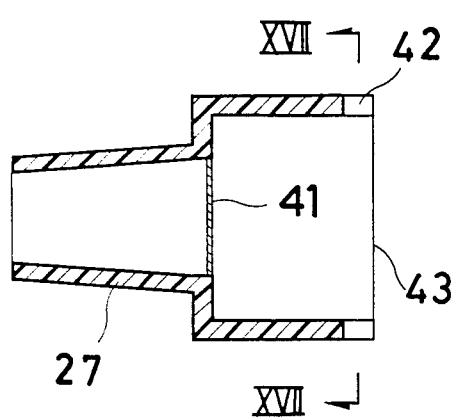
FIG. 17a is a sectional side elevational view of an embodiment in which the pressing surface of the end plug is opened.
Figure 17B:
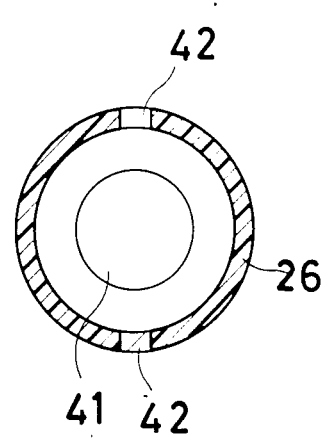

When a specifically large thrusting force is required for the puncture, a flange 46 capable of retaining the second finger (forefinger) and the third finger (middle finger) is provided on the catheter hub 45 as shown in FIG. 16, and the end plug 24 described heretofore having at least one vent 47 is attached to this puncture needle hub 23, so that the puncture needle assembly is held stably to permit an application of the large thrusting force. FIG. 16 illustrates the semiassembled condition with the needle 22 slightly extracted into the catheter 44.

According to the second aspect of the invention, the end surface of the air vent plug opposite to the puncture needle hub, closed or opened, is used as the pressing surface on which the puncturing pressure is applied by thumb. An air-permeable blood-tight member provided in an air vent plug cooperates with the puncture needle hub in defining a small chamber for confirmation of the blood flush back. An opening to the atmosphere is formed at least in the surface of the air vent plug other than the pressing surface at the downstream side of the air-permeable blood-tight member as viewed in the direction of flow of blood and air during flushing back so that the through bore in the puncture needle is communicated with the atmosphere through the air-permeable blood-tight member. Therefore, the air in the small chamber can be relieved to the atmosphere through the opening even though the end surface of the air vent plug is pressed by the thumb for the puncturing of the blood, so that the blood can flush back without any resistance by air. In addition, the puncture needle hub made of a transparent or translucent material permits an easy observation of the flushing back blood and, hence, a confirmation of correct puncture of the desired blood vessel burried under the tissue. The air-permeable blood-tight member can be formed of a membrane filter or a sintered body which has superior resistance to permeation of blood and can be manufactured easily. When the air-permeable blood-tight member is formed of a member with slit or slits, the air-permeable blood-tight member can be formed as a unit with the air vent plug advantageously, unlike the case of the filter. The application of large thrusting force by placing the thumb on the end surface of the air vent plug is necessary when the puncture needle aims at a blood vessel deep in the tissue, particularly an artery. It will be understood that the aforementioned problem concerning the operation of the conventional puncture needle assembly can overcome by the puncture needle assembly of the second aspect of the invention.

The puncture needle assembly of the second aspect can be used in combination with an outer catheter for making the catheter indwell in the blood vessel. Thus, the puncture needle assembly of the second aspect of the invention has a large variety of use. The opening is formed in the peripheral wall of the air vent plug. Alternatively, the air vent plug is formed to have a step in its outer peripheral surface such that the portion adjacent to the puncture needle is smaller in diameter, and the opening is formed in the axial end surface of the step facing the beveled point of the needle. In these cases, even if the open end surface of the air vent plug as shown in FIG. 9 is closed by the thumb for exerting the puncturing pressure, there is almost no chance of closing of the opening by the finger, so that the air in the puncture needle and the small chamber is relieved without fail to permit the flush back of the blood. In addition, the formation of the opening in such positions is relatively easy to implement.

What I claim are:

1. A method for inserting a puncture needle assembly into a relatively deep blood vessel, said puncture needle assembly comprising a puncture needle having a point and being provided with a through bore, a transparent or translucent puncture needle hub fixed to the end of said puncture needle opposite to said point; and an air vent plug adapted to be detachably connected to said puncture needle hub in a liquid-tight manner; said air vent plug having a pressing surface at the most distal end surface thereof opposite to said puncture needle and adapted to be engaged by a hand of a user for transmitting a puncture force from a hand of a user in the axial direction of said puncture needle via said pressing surface, said pressing surface being ring-like and defining an opening which is open to the atmosphere, and said air vent plug having a side peripheral wall adjacent said pressing surface; said air vent plug including means adapted to form, when it is connected to said puncture needle hub, a passage providing communication between said through bore of said puncture needle and the atmosphere, said passage being opened to the atmosphere through at least one side opening recessed from said pressing surface and opening into the side peripheral wall of said air vent plug, said at least one side opening being sized so as to be left uncovered by any part of the hand of the user when said puncture force is applied by said hand to said pressing surface at said distal end of the air vent plug; and an air-permeable blood-tight member disposed in said passage at the upstream side from said at least one side opening, said through bore of said puncture needle being in communication with the atmosphere through said air-permeable blood-tight member and said at least one side opening in said air vent plug;

said method comprising the steps of:
holding said puncture needle assembly in the hand of a user;
putting a portion of the hand of the user on said pressing surface of said air vent plug;
thrusting, by the user's hand, the puncture needle assembly via an applied thrusting force on said air vent plug in the axial direction of said puncture needle assembly to transmit a puncture force from the user's hand to said air vent plug and hence to said puncture needle while leaving open and uncovered said at least one side opening of said air vent plug; and
directing the puncture needle of said puncture needle assembly to puncture the blood vessel responsive to said thrusting by the user.

2. The method of claim 1, wherein said portion of the hand of the user which is put on said pressing surface of said air vent plug to apply said thrusting force is the thumb of the user.

3. The method of claim 1, wherein after said puncture needle assembly punctures the blood vessel, blood is flushed back into said passage via said through bore of said puncture needle, and air in said puncture needle and in said passage is forced out by the blood flowing into said passage through said air-permeable blood-type member.

4. A puncture needle assembly for puncture into relatively deep blood vessels, comprising:
a puncture needle having a point and being provided with a through bore, a transparent or translucent puncture needle hub fixed to the end of said puncture needle opposite to said point; and
an air vent plug adapted to be detachably connected to said puncture needle hub in a liquid-tight manner,
said air vent plug having a pressing surface at the most distal end surface thereof opposite to said puncture needle and adapted to be engaged by a hand of a user for transmitting a puncture force from a hand of a user in the direction of said puncture needle via said pressing surface, said pressing surface being ring-like and defining an opening which is open to the atmosphere, and said air vent plug having a side peripheral wall adjacent said pressing surface,
said air vent plug including means adapted to form, when it is connected to said puncture needle hub, a passage providing communication between said through bore of said puncture needle and the atmosphere, said passage being opened to the atmosphere through at least one side opening recessed from said pressing surface and opening into the side peripheral wall of said air vent plug, said at least one side opening being sized so as to be left uncovered by any part of the hand of the user when said puncture force is applied by said hand to said pressing surface at said distal end of the air vent plug, and
an air-permeable blood-tight member disposed in said passage at the upstream side from said at least one side opening, said through bore of said puncture needle being in communication with the atmosphere through said air-permeable blood-tight member and said at least one side opening in said air vent plug.

5. A puncture needle assembly according to claim 4, wherein said air-permeable blood-tight member comprises a filter permeable to air but impermeable to blood.

6. A puncture needle assembly according to claim 4, wherein said air-permeable blood tight member comprises a member having at least one slit formed therein which is permeable to air but impermeable to blood.

7. A puncture needle assembly for puncture into relatively deep blood vessels, comprising:
a puncture needle having a pointed end and a through bore,
a puncture needle hub fixed to the end of said puncture needle opposite to said point,
an air vent plug adapted to be detachably connected to said puncture needle hub in a liquid-tight manner,
an outer catheter having a through bore for receiving said puncture needle therein, and
a catheter hub fixed to the proximal end of said outer catheter and attachable to said puncture needle hub,
said air vent plug having a pressing surface at the most distal end surface thereof opposite to said puncture-needle hub and adapted to be engaged by a hand of a user for transmitting a puncture force from a hand of a user in the direction of said puncture needle via said pressing surface, said pressing surface being ring-like and defining an opening which is open to the atmosphere, and said air vent plug having a side peripheral wall adjacent said pressing surface, said air vent plug including means adapted to form, when it is connected to said puncture needle hub, a passage providing communication between said through bore of said puncture needle and the atmosphere, said passage being opened to the atmosphere through at least one side opening recessed from said pressing surface and opening into the side peripheral wall of said air vent plug, said at least one side opening being sized so as to be left uncovered by any part of the hand of the user when said puncture force is applied by said hand to said pressing surface at said distal end of the air vent plug, and an air-permeable blood-tight member disposed in said passage at the upstream side from said at least one side opening, said through bore of said puncture needle being in communication with the atmosphere through said air-permeable blood-tight member and said at least one side opening in said air vent plug.

8. A puncture needle assembly according to claim 7, wherein said air-permeable blood-tight member comprises a filter permeable to air but impermeable to blood.

9. A puncture needle assembly according to claim 7, wherein said air-permeable blood-tight member comprises a member having at least one slit formed therein which is permeable to air but impermeable to blood.

* * * * *

UNITED STATES PATENT AND TRADEMARK OFFICE
CERTIFICATE OF CORRECTION

PATENT NO. : 4,682,980
DATED : July 28, 1987
INVENTOR(S) : T. SUZUKI

It is certified that error appears in the above-identified patent and that said Letters Patent is hereby corrected as shown below:

IN THE ABSTRACT, line 13, "catheter, hub" should read
-- catheter hub, --

Column 2, line 44, "allow of the" should read -- allow the --
Column 3, line 20, "supproting" should read -- supporting --
Column 8, line 43, "needle, 23" should read -- needle 23, --
Column 8, line 50, "opend" should read -- opened --
Column 8, lines 66-67, "accordnace" should read -- accordance --
Column 11, line 29, "blood flushed" should read -- blood is flushed --
Column 11, last line,"with the minimum" should read -- with minimum --

Signed and Sealed this

Twenty-third Day of February, 1988

Attest:

DONALD J. QUIGG

Attesting Officer

Commissioner of Patents and Trademarks